United States Patent [19]
Stern

[11] 3,972,791
[45] Aug. 3, 1976

[54] FRACTIONATION OF PROTEINS BY ELECTRICAL MEANS

[76] Inventor: Harold Stern, Llewellyn Park, West Orange, N.J. 07052

[22] Filed: May 6, 1974

[21] Appl. No.: 467,115

[52] U.S. Cl.......................... 204/180 P; 204/180 R
[51] Int. Cl.$^2$........................................... B01K 5/00
[58] Field of Search ............ 204/180 P, 301, 180 R

[56] References Cited
UNITED STATES PATENTS

| | | | |
|---|---|---|---|
| 3,325,389 | 6/1967 | Parsi et al. | 204/180 P |
| 3,330,749 | 7/1967 | Kuwata et al. | 204/180 P |
| 3,497,438 | 2/1970 | Badgley | 204/180 R |
| 3,767,548 | 10/1973 | Okada et al. | 204/180 P |
| 3,829,370 | 8/1974 | Bourat | 204/180 P |

Primary Examiner—John H. Mack
Assistant Examiner—A. C. Prescott
Attorney, Agent, or Firm—Roland Plottel

[57] ABSTRACT

A process for the fractionation of liquid solutions of protein mixtures which includes the steps of subjecting such solutions to electrodialysis in the pH range 4.8 to 6, until desalting of the solution commences, said electrodialysis being conducted at temperatures below 15°C; and continuing said electrodialysis until the specific resistance of the mixture exceeds 1000 ohm-cm whereby a fraction of said protein mixture precipitates; and recovering the dialysate. Another aspect of the invention is an albumin concentrate for use in the preparation of plasma extenders, having at least 90% albumin, free from salts, euglobulins and euglobulin-like materials.

20 Claims, 3 Drawing Figures

FRACTIONATION OF PROTEINS BY ELECTRICAL MEANS

FIELD OF THE INVENTION

This invention relates to the separation of complex protein mixtures and more particularly to the fractionation and partial resolution of such mixtures by combinations of electrodialysis and at least one of the following steps: forced-flow electrophoresis, electrodecantation and alcohol precipitation.

BACKGROUND OF THE INVENTION

Biological fluids usually contain a mixture of several proteins, and one of the major achievements of modern biochemistry is to have devised methods for their separation. Best example if blood plasma or serum, where methods are available for identification and separation of at least 25 major protein components (Schultze and Heremans: Molecular Biology of Human Proteins, Elsevier, 1966). Other examples of naturally occurring complex proteins mixtures is milk or whey, urine, spinal fluid, egg white, etc.

For the purpose of the present disclosure, it is helpful to define the following protein nomenclature, the classification being based on their solubility in a variety of solvents: (1) albumin is the major protein component of plasma, serum, and egg white, and is characterized by being soluble both, in half-saturated ammonium sulfate and in distilled water; (2) globulins are those proteins of plasma or other biological fluids which precipitate in half-saturated ammonium sulfate; (3) euglobulins are those globulins which are not only precipitated in half-saturated ammonium sulfate, but also in deionized water, as they apparently need some salts to be soluble. Obviously, this classification is arbitrary, though widely used in protein chemistry, as the solubility of all proteins depends also on the pH of the solution, temperature, and other solutes present, such as alcohol; (4) euglobulin-like materials; the term "euglobulin-like" is used herein for those proteins which precipitate in deionized aqueous solutions only in presence of various amounts of alcohol. These proteins are not true euglobulins, being soluble in deionized water in absence of alcohol, yet they possess some of the characters of the euglobulins, being solubilized by even low concentrations of salts.

It will further help to define, for the purposes of this invention, the following electrical membrane processes:

1. Electrodialysis is primarily used for the desalting of aqueous solutions. Uusally, this is accomplished by means of ion-selective membranes, said membranes allowing preferential passage of either positively or negatively charged ions, as described in a variety of patents including U.S. Pat. Nos. 2,694,680, 2,848,402, 2,860,091, 2,777,811. The usefulness of this technique for the separation of proteins has not previously been recognized. Ion-selective membranes can also be substituted by essentially electrically neutral membranes, with inclusion of polyelectrolytes into certain compartments, these polyelectrolytes becoming polarized along the membranes under the influence of an electrical field, thereby conveying to the neutral membranes an element of ion-selectivity as taught in U.S. Pat. Nos. 3,677,923 and 3,725,235. In other electrical membrane processes, discussed in the following two sections, some electrodialysis is unavoidably superimposed to other effects sought, being a direct result of the passage of electrical current. For the purpose of the present invention, the term electrodialysis will be reserved to these electrical processes, the primary purpose of which is desalting, preferentially accomplished either with ion-selective membranes or with the use of polyelectrolytes.

2. Electrodecantation is an electrical process for concentration and separation of a variety of colloids including proteins as taught in U.S. Pat. Nos. 2,057,156, 2,292,608, 2,762,770, 2,800,448, 2,801,962. These teach devices which contain a multitude of essentially electrically-neutral membranes in a parallel array, the colloids or proteins accumulating under the influence of the electrical current or fields in the immediate neighborhood of said membranes and are decantable along said membranes as a result of density gradients. An analogous method is sometimes referred to as electrophoresis-convenction (in U.S. Pat. No. 2,758,966), where usually only a single pair of electrically neutral membranes is employed for the purpose of creating electrodecantation in the protein solution. These techniques have been widely used for protein fractionation, principally for preparation of gamma globulins, these proteins of plasma being isoelectric and not decanting. This technique has not been taught for the preparation of serum albumin, the most mobile of plasma proteins (in terms of electrophoresis). Among the objectives of the present disclosure is to teach utilization of such techniques for fractionation for the preparation of serum albumin.

3. Forced-flow electrophoresis includes devices similar to those for electro-decantation, which also utilize a parallel array of electrically neutral membranes, but the partitions are located between adjacent pairs of membranes. Such partitions permit better control of flow patterns within the apparatus, and also act as diffusion barriers. Two such electrophoresis devices are described in U.S. Pat. Nos. 2,878,178 and 3,079,318, and the technique also is described as "forced-flow electrophoresis" by M. Bier; "Electrophoresis", Academic Press, 1959, page 295.

The processes of electrodecantation and forced-flow electrophoresis are similar in principle and results and for purposes of convenience will be often referred to herein as electrofield separations. As set forth below they may be used interchangeably.

The most important protein products of commerce are those obtained from human or animal plasma or serum. Two such proteins, serum albumin and gamma globulins, either from human or animal origin will be used as the principal examples but the scope of this invention can also be applied to other biological fluids or other proteins without modification. The present commercial methods of obtaining these fractions are based on alcohol fractionation, a process developed by Cohn et al and described in U.S. Pat. Nos. 2,390,074, 2,770,616. This technique is essentially based on sequential precipitation of various protein fractions by alcohol, under controlled conditions of temperature, alcohol content, pH, and salt content as summarized by C. A. Janeway, Adv. in Internal Med. 3, 295, 1949. This technique requires a large installation, the yield of certain fractions is low, it requires prolonged exposure of proteins to high alcohol content, which has a denaturing effect on some protein fractions. The technique is also limited to production of certain fractions of plasma only; other protein fractions are not recoverable in sufficient states of purity.

THE INVENTION

The present invention relates to the fractionation and partial resolution of protein mixtures, principally mixtures such as but not exclusively plasma, serum, or their derivative fractions, using one or more of the electrical processes above defined, either alone or in combination with each other, and in combination with alcohol fractionation. The fractionation scheme of this invention permits far greater flexibility in terms of fractions obtainable as the electrical processes can replace some or all of the fractionation steps in conventional alcohol fractionation, resulting in substantial savings of money, time, installation costs, and provide increased yield of products. More specifically, the invention includes:

1. the process of fractionation of proteins including plasma or plasma fractions, comprising causing the precipitation of an euglobulin fraction by means of electrodialytic desalting under controlled conditions of temperature, pH, and conductivity and recovering the dialysate.
2. the process of fractionation of proteins including plasma or plasma fractions, comprising precipitation of an euglobulin-like fraction by means of electrodialytic desalting under controlled conditions of temperature, pH, conductivity, and alcohol content.
3. process of fractionation of proteins including plasma or plasma fractions, comprising preparation of an euglobulin-like precipitate by electrodialytic desalting under controlled conditions of temperature, pH, conductivity, and alcohol content, followed by selective dissolution of albumin-enriched fraction by re-adjustment of temperature, pH, conductivity, or alcohol content.
4. process of plasma fractionation, comprising the steps including a first precipitation by alcohol, a second step of electrodialytic desalting of the supernatant of said first precipitation, said second step causing precipitation of an euglobulin-like fraction, an elective third step comprising selective dissolution of an albumin rich fraction from said euglobulin-like precipitate, and a last step of alcohol precipitation of an albumin-rich fraction from the combined supernatants of electrodialytic desalting step or, alternatively from the combined supernatants of the second step and the elective third step of fractionation.
5. process of improving fractionation of protein mixtures by electrodecantation or forced-flow electrophoresis, comprising the reduction of their salt content through prior electrolytic desalting, said desalting causing also precipitation of euglobulins or euglobulin-like materials.
6. process of improving fractionation of protein mixtures by electrodecantation or forced-flow electrophoresis, comprising the reduction of their salt content through prior desalting, and subsequent addition of a buffering salt, said buffering salt being an ampholyte such as glycine, said desalting causing also precipitation of euglobulins.
7. process of plasma fractionation, comprising a first precipitation by alcohol, a second step of electrodialytic desalting of the supernatant of said first precipitation, said second step causing precipitation of an euglobulin-like fraction from said euglobulin-like precipitate, and a last step comprising the selective concentration of an albumin-rich fraction by means of electrodecantation of forced-flow from the supernatant of the desalting step or alternatively the combined supernatants from the desalting and the elective third step of fractionation.
8. products of manufacture suitable for use as plasma expander, and comprising at least 90% of albumin, obtained by above processes, in particular by processes 4 or 7.

These and other aspects of the invention will become clear from the following detailed description.

DETAILED DESCRIPTION

Figure 1:
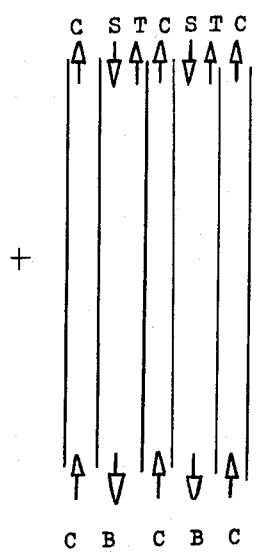

A. Electrodialysis is widely used for desalting of aqueous solutions. In the field of proteins it has received usage in desalting of milk, whey (U.S. Pat. Nos. 3,433,726; 3,447,930; 3,595,766; 3,757,005; 3,754,650), but these patents have no relations to present invention, as they are only concerned with reducing the salt content of whey, rather than with the incorporation of the desalting process into a complex scheme of fractionation.

It is also well known that desalting causes precipitation of euglobulins. The U.S. Pat. Nos. 2,669,559; 2,761,809; 2,761,811; 3,234,199 and 3,429,867 disclose the application of desalting by means of ion exchange resin beds, for purposes of plasma fractionation, but this process has too limited flexibility in terms of products obtainable to be of significant practical value. In addition, ion exchange columns are difficult to maintain in suitable state of cleanliness and sterility necessary for protein fractionation.

It is the essence of this invention that it was discovered that electrodialytic desalting can be a valuable tool in an overall scheme of plasma fractionation, if used in conjunction with other techniques, because the results of combining various techniques together increases the usefulness of each in a previously unsuspected manner. Specifically:

Addition of various amounts of alcohol to desalted proteins causes additional precipitation of unstable or euglobulin-like proteins. The process is not quite identical to alcohol fractionation of proteins, because the quality and composition of the precipitated fraction if inordinately sensitive to temperature, pH, and smallest quantities of electrolyte, characteristic of all euglobulin fractionations. The value of this discovery is particularly significant in as much as the current scheme of alcohol fractionation separates, in the first step, a so-called Cohn fraction II and III, the precipitate comprising most of the gamma globulins. The supernatant contains approximately 20% of alcohol already, and if this is now desalted, one obtains a precipitation of euglobulin-like fraction which contains most of the remaining globulins of plasma (called alpha and beta globulins), which are undesirable in the preparation of serum albumin. Moreover, because of the danger of hepatitis infection, it is highly desirable to prepare the gamma globulins in the time-honored manner by alcohol fractionation, the resulting product being non-infectious. Thus the use of electrodialytic desalting fits into the present scheme of fractionation by providing a gamma globulin product prepared by presently acceptable methods, and additionally offering a shortcut in albumin preparation. Hepatitis is not a problem in albumin preparations, as they can be pasteurized by heat treatment as taught in U.S. Pat. Nos. 2,705,230; 2,958,628.

In addition, because of the inordinate sensitivity to temperature, pH and ionic strength of the composition of euglobulin fraction, this fraction can easily be used to provide a variety of subfractions, yielding products useful for the preparation of other plasma fractions.

The euglobulin-like fraction obtained at 20% alcohol content also contains a significant amount of albumin which can be recovered by selective dissolution, as shown in the examples. Again from such a source a further variety of fractions can be obtained. It is not necessary to first separate the euglobulin-like fraction from its supernatant to effectuate selective dissolution, but the pH, temperature, conductivity, or alcohol content of the desalted protein mixture can be adjusted in a multitude of ways, again to be explained in the examples, showing that a new and versatile tool of fractionation is obtained when combining the before-mentioned factors of alcohol content, pH, conductivity and temperature.

It is also not necessary that the first step in the fractionation be an alcohol precipitation step, say the Cohn fraction II and II separation. This procedure only fits best in the present scheme of gamma globulin preparation. But it is also possible to first desalt the plasma, separate or not separate the euglobulins formed, and then add alcohol to the desalted plasma, to bring about additional precipitation of euglobulins-like fraction. This euglobulin-like fraction precipitates already at 10% alcohol content, while the Cohn fractionation requires twenty percent of alcohol content for its first step, thus significant amounts of alcohol can be saved. This fractionation scheme is particularly attractive if only albumin is desired, and not gamma globulins, as is the case with many animal sera, where albumin is the most significant product of commerce. It is also useful if separation of the so called macro-globulins or IgM immunoglobulins is desired. These are presently lost in the scheme of Cohn alcohol fractionation, but can easily be recovered in the first euglobulin fraction, being insoluble even in absence of alcohol.

Optimal precipitation of euglobulins or euglobulin-like proteins occurs at their isoelectric points, which is the point of their least solubility. It is characteristic of properly carried out electrolytic desalting procedures that the final mixture automatically comes to the pH corresponding to the average isoelectric point of proteins in the mixture, as all free ions are removed and only proteins are retained. In the case of plasma, this corresponds to a pH of 5.3 ± 0.2 pH units. Because of protein-protein interaction, there is co-precipitation of several proteins, but the composition of the precipitate can be altered and modified by adjusting the pH to a range of pH values from pH 6 to 4.8, thereby significantly altering the composition of the precipitate, and permitting selective precipitation of certain proteins, including the aforementioned macroglobulins.

Precipitation of euglobulins in plasma begins at a specific resistance of above 1,000 ohms.cm, but increases progressively until maximum desalting. For best fractionation of euglobulins or euglobulin-like fractions, a resistance in excess of 50,000 ohms.cm is necessary; most of the fractionations having been carried out in the range of between 50,000 and 200,000 ohms-cm.

Temperature plays a significant role in the precipitation of the euglobulin-like fraction. Most of the fractionation is carried out in the temperature range of below 5°C, but subfractionation of the euglobulin-like fraction can be carried out at temperatures from about 15°C and lower.

Summarizing, then, the optimal fractionation of proteins by electrodialytic desalting is obtained within the following narrow ranges of conditions: temperature below 15°C, pH 5.3 plus minus 0.2, resistance above 100,000 ohms-cm. The influence of these parameters will be made more specific in examples of actual fractionation.

The equipment for carrying out electrodialytic fractionation is not of critical design, and several commercial instruments can be utilized. Most of the experiments reported here were carried out with instruments obtained from the Ionics Corp., B Watertown, Mass. It is important to properly select paired ion exchange membranes which will cause proportionate removal of positively and negatively charged ions from solution, thus avoiding excessive changes in pH values. This has been obtained with the Ionics Corp. membranes. Other instruments would no doubt give equally good results, and in some of the work home-made apparatus was used, similar to that described in U.S. Pat. Nos. 3,079,318 and 3,677,923. Desalting can also be carried out using the process described in the just mentioned U.S. Pat. No. 3,677,923, thus avoiding the necessity of using ion-exchange membranes.

The protein solution is continuously circulated through the electrodialysis apparatus, refrigerated by means of heat exchangers, and a d.c. electric field superimposed across the membranes to cause electrodialysis. The electrolyte brine bathes the alternate sides of the membranes, and gradually becomes more salt concentrated as it receives the salts from plasma. This brine can be of any usually suitable composition. Its composition or conductivity is not critical to the process.

In most fractionations using ion exchange membranes, a solution of about 0.5 gms/liter of sodium chloride was employed. Other electrolyte solutions have been equally acceptable.

In experiments based on electrically neutral membranes, the "brine" was a 0.2% solution of polyacrylic acid, adjusted to pH 6 with sodium hydroxide. For best temperature control, the brines are also cooled by cooling means such as heat exchangers.

With a properly balanced system, the pH of the plasma gradually decreases toward its average isoelectric point of pH 5.2 ± 0.2. Precipitation begins at a specific resistance of about 1,000 ohms-cm, and a pH of about 5.6. If the starting product is not plasma, but an alcohol-precipitation-derived fraction thereof, precipitation occurs when a resistance of about 6,000 ohms-cm is reached, as some of the euglobulins have already been eliminated. In either case, precipitation is most complete at highest possible desalting, when the resistance is above 100,000 ohms-cm.

The protein should be circulated vigorously through the appropriate chambers of the electrodialytic apparatus, in order to provide maximum turbulence within the apparatus. This is well established in the art of electrodialysis. A circulation pressure of 25 lbs/sq. in. was employed in most experiments. This turbulence is also necessary to prevent deposition of precipitating proteins within the apparatus, thus clogging of its channels of flow.

In order to minimize the clogging problem, it is also possible to install a continuous centrifuge in the flow circuit of the protein solution.

Precipitation of euglobulins is rapid, and their complete centrifugation is obtained at relatively low speeds of centrifugation, 2,000 rpm being sufficient. This expedient has certain advantages, as it enables fractionation of the euglobulins as they are being formed, by collecting and segregating the precipitates separately at the different pH or resistance values. It is also advantageous to insert into the pathway of protein circulation suitable monitoring instruments for automatic or operator actuated monitoring for control of pH, resistance, and temperature during the desalting process.

Should clogging of any part of the apparatus become apparent, as indicated by a sudden increase of pressures, this can be easily remedied by adding a suitable alkalinizing agent, such as sodium hydroxide solution in amounts to raise the pH of the protein solution above pH 6. This causes rapid dissolution of all precipitates. This declogging does not cause great delay in the overall process of desalting. Electodialysis of sodium ions is much more rapid than that of many other ions in the protein solution. The overall time requirement for complete desalting is mainly limited by these slower electrodialysing ions and not by the sodium ions. Thus it is possible to completely desalt the protein mixture, then add sufficient alkali to redissolve all the precipitates (which of course, decreases the resistance), and then obtain a final product in a further, final pass through the electrodialyzer, by which the added sodium hydroxide will be removed. This avoids accumulation of the precipitate in the apparatus. Most of the precipitation being sufficiently time-delayed, it occurs only after exit from the dialyzer.

Another method to avoid precipitation and clogging within the apparatus is by a periodic reversal of current polarity.

Because of the requirement of numerous recirculations of the plasma through the apparatus before complete desalting is obtained, the process is essentially a batch process. However, it can be rendered semi-continuous, by a sequenced operation wherein an intermediary vessel receives a portion of the total protein solution, this portion is then completely desalted by repeated circulation through the electrodialyzer, and then replaced by a new batch, as is well known in the art of process automation. By sequencing the passage of the protein solution through successive dialysis chambers the salt content in each successive chamber is reduced until the final chamber where the salt content is at a minimum.

The power requirement for the electrodialysis is not critical. Most of the experiments have been started with a current density of about 0.03 amps/cm$^2$, necessitating less than 25 volts/cm. As the resistance of the electrodialyzer progressively increases, due to increased resistance of the protein solution, the voltage is gradually increased up to 100 volts/cm. Final current density is low, usually less than about 0.03 amps/cm$^2$. The main limitation to the power is that is causes heating of the solution. Control of the total power input is based upon monitoring the temperature of the effluent streams. The temperature can be maintained below any desired value, consonant with the stability and sanitary management of the protein solutions, i.e., it can be maintained throughout the experiment at below about 5° or 10°C.

Sanitation is of utmost importance in protein fractionation. The complete electrodialyzer apparatus, all connections, tubing, pumps, etc., are sanitized in situ by conventional procedures, such as rinsing with dilute sodium hydroxide, hydrochloric acid, hypochlorite or other suitable agents. Rinsing with sodium hydroxide is preferred as it is also an effective means of removing precipitated proteins.

B. Both, forced-flow electrophoresis and electrodecantation have been used for fractionation of plasma proteins as taught in U.S. Pat. Nos. 2,801,962; 2,878,178; 3,079,318. The usual objective has been the isolation of gamma globulin. The reason for this focusing on gamma globulin is that these methods are easily and directly applicable because gamma globulin is isoelectric or near isoelectric over a relatively broad pH range around neutrality. The above two methods essentially differentiate only between isoelectric and mobile components. In both methods, the mobile components are brought to electrodecant, and the supernatant is composed mainly of isoelectric or near isoelectric components, which (by definition of the term "isoelectric" — having equal positive and negative charge, i.e. having zero net charge) are not affected by the applied electric field. The decanting fraction contains most of the albumin, which is the electrophoretically most mobile major component of plasma. Albumin so fractionated however is heavily contaminated by globulins of intermediate mobility, broadly referred to as alpha and beta globulins.

These methods of forced-flow electrophoresis or electrodecantation have not yet found application for commercial production of gamma globulins or any other plasma fractions. The reasons for it are numerous, and include:

1. Gamma globulin is not in short supply. More albumin is required than gamma globulins.

2. The Cohn alcohol fractionation method yields a product free of infectious hepatitis agents. It is not yet certain whether other methods, such as the above electrical processes, would consistently yield an equally safe product. As a result, many legal specifications require the alcohol fractionation process. In view of the abundance of this product, there are few incentives to change the process.

Equally important are, however, some purely technical shortcomings of these two electrical processes, which are overcome by the present invention:

1. Plasma contains a number of relatively unstable proteins, which precipitate readily, either as a result of low inherent solubility or because of denaturation. As a result, when plasma is used, longevity of the multimembrane assemblies, used in these two electrical processes, is limited because membrane fouling occurs as a result of precipitation. As the assembly of these multimembrane apparatus is an important cost element, this renders the processes expensive. By practice of this invention this problem is completely eliminated by either of the two treatments discussed in previous sections: (a) alcohol prefractionation resulting in the so-called Cohn fraction II + III supernatant, or (b) the electrodialytic desalting. Either of these two initial fractionation steps eliminate the unstable proteins, and no traces of membrane fouling is observed.

2. Though the membranes employed in these two processes of electrophoresis and electrodecantation are essentially electrically neutral, their character is altered as a result of protein polarization along the membranes caused by the electrical field, as observed and explained in U.S. Pat. No. 3,677,923. An element of electrodialysis is thus superimposed upon the fractionation process, and there is partial desalting of the "isoelectric" fraction causing premature precipitation. Euglobulins tend therefore to precipitate, and contribute to the aforediscussed problem of membrane fouling. Obviously, this problem is avoided in the present invention, as all euglobulins have been eliminated in the electrodialytic desalting.

3. Plasma has a high salinity, corresponding approximately to 0.9% sodium chloride. This severely limits the electrical field which can be applied because the Joule heating caused by the electrical field is proportional to the conductivity, i.e. salt content, of the processed fluid. As a result, the processing rates are low (being again proportional to the field applied), and, at best, marginal, from a commercial point of view. Dilution has been advocated to remedy the high salt content in U.S. Pat. No. 2,878,178, Example 3 but this is, at best, a palliative effect, and it commensurately increases the volumes to be processed.

In the present invention, this problem is entirely eliminated. The effluent of the electrodialytic desalting has no residual salts — and thus excessive heating as a result of the electrical field, is avoided. Heating is deleterious, of course, because of purely sanitary considerations as well as causing chemical degradation. Higher electrical fields can be applied by the process of this invention thus resulting in faster production rates, making the process economically more attractive.

4. Most of the salt content in plasma is actually sodium chloride, which has no buffering action at the pH range where protein fractionation is carried out. Thus, the pH of processed fluid is poorly controlled with resulting uncertainty regarding the actual sharpness of the fractionation, as the electrophoretic mobility of proteins are strongly pH dependent. The addition of suitable buffers to untreated plasma can ameliorate the situation, but is also adds to the overall conductivity of the solution, which, as outlined above, is highly undesirable. Prior desalting of the liquid being processed permits the suitable addition of any number of buffers, such as phosphate, tris (hydroxymethyl) aminomethane, glycine, and others, which exert their maximum buffering action in the desired pH range, while maintaining the conductivity of the medium at an order of magnitude lower than that of untreated plasma. For this purpose, particularly suited and preferred are amphoteric buffer salts, for example glycine, which while stabilizing the pH, do not contribute significantly to the conductivity of the medium. Other amphoteric substances are the various other amino acids, including alanine, or di or tri-peptides, including glycylglycine and glycyl-glycyl-glycine. Such products are readily available in commerce, and provide a sutiable range of isoelectric points.

5. Prior investigators have been unable to use techniques such as forced-flow electrophoresis of electrodecantation for the production of any other plasma fractions except gamma globulin. Albumin, in particular, was not possible to prepare in sufficient purity for use as a plasma expander, by any of the previous investigators. This has been remedied in the present invention, as a result of:

a. elimination of the precipitate of the Cohn II and III fractionation steps;
b. the precipitation of euglobulins or euglobulin-like materials by electrodialytic desalting;
c. by the improved conditions prevailing during the fractionation as a result of the lower salt content and introduction of appropriate buffer into the processed fluid, as explained under 3 and 4 above; and
d. finally, by permitting the use of special conditions during the fractionation itself.

These special conditions (d) merit more detailed discussion:

In either electro-decantation or forced-flow electrophoresis, the influent stream is divided into two fractions. The most mobile components are segregated into the decanted fraction, at the bottom of the membrane-defined compartments. These include the desired albumin fraction. The less mobile or isoelectric components, are segregated to the top of the membrane-defined compartments. The relative distribution of components in the two effluents, which will be referred to, for brevity's sake, hereinafter as the top and bottom effluents, is a function of many factors, including the applied field, conductivity, temperature, relative concentrations and the mobility of each component of the mixture.

As a rule, at constant top flow, the slower the bottom flow the higher its total protein content. It has now been discovered that paralleling this increased concentration of protein, there is also an increased purity of the albumin fraction, recovered in the bottom effluent. For optimum protein concentration, it is necessary to maintain the bottom effluent at a concentration between 15–25% total protein content. This is preferably achieved by maintaining the top to bottom flow rates in a ratio of between 8:1 and 15:1, depending on the concentration of the starting supply.

Forced-flow electrophoresis and electrodecantation, according to this invention, have been performed using the components of equipment as described in U.S. Pat. No. 3,079,318. Three different modes of operation have been successfully used. These are schematically illustrated in the figures which are schematic presentations of the side views of the membranes and filters used in this type of apparatus. The figures do not show the spacers maintaining the components in their proper place, which may include the inlet and outlet means. The solid lines represent membranes which are of the type generally used in passive dialysis, i.e. electrically neutral membranes, such as regenerated cellulose sold under the trade name "Visking" by Union Carbide. The broken line represents filters. These can be of many different types, including filter paper (for instance Whatman No. 54), microporous filters as sold by the Millipore or Gelma Corp., or certain type of battery separator elements as utilized by the Mallory Corp.

The essential difference between filters and membranes, above described, is that filters are permeable to proteins and permit gross liquid flow through them. Membranes, on the other hand retain proteins and do not allow gross liquid flow through them, but only slow ultrafiltration. The arrows in the figures indicate the direction of the flow of the liquids through the apparatus.

Figure 2:
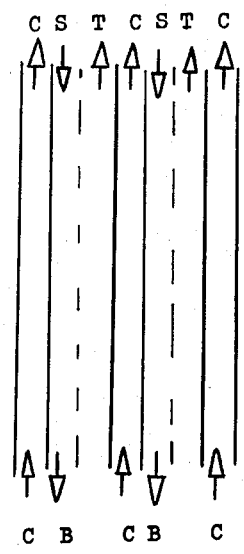
Figure 3:
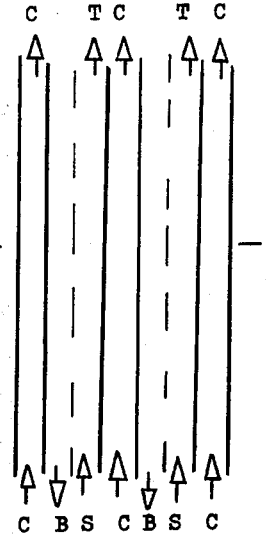

FIG. 1 illustrates the electrodecantation mode, while FIGS. 2 and 3 illustrate two modalities of forced-flow electrophoresis, differing in the location of the feed inlet. These two modalities differ little in their results and may be used interchangeably.

The figures also illustrate the essential difference between electrodecantation and forced-flow electrophoresis. In forced-flow electrophoresis the filters separate each electrophoretic compartment into two subcompartments. The filters act, essentially as frictional boundaries between downward and upward flowing portions of liquid, and thus add substantially to the efficiency of the procedure. While, therefore, forced-flow electrophoresis is the preferred technique, essentially similar results are achieved by electrodecantation.

A desirable element in the process, though not essential, is the separation of individual electrophoretic compartments from each other by channels for the flow of suitable electrolyte. The electrolyte primarily provides for maximum of internal cooling of the apparatus, and to this purpose, the electrolyte is circulated through an external refrigerating heat exchanger.

It is preferred that this electrolyte be a buffer, and that the same considerations apply to it as discussed above with regards to the buffering of the protein solution being processed. Thus, phosphate, glycine, sodium octanoate, or other buffers can be utilized. The electrical conductivity of the buffer should be of the same order as the conductivity of the protein solution being processed to assure a relatively uniform electric field throughout the apparatus. This buffer also plays an additional important role in the fractionation of alcohol-containing protein solutions. By diffusion through the membranes, a substantial part of the alcohol can be eliminated from the effluent protein solutions, where it is undesirable.

EXAMPLE I

This example demonstrates the difference between euglobulins and euglobulin-like materials, i.e. the difference between precipitation of desalted proteins in absence or presence of 10% alcohol. Two liters of bovine plasma were desalted in an electrodialysis cell consisting of two pairs of cationic and anionic membranes, 9 × 10 inches, until the specific electrical resistance of 200,000 ohms-cm, at pH 5.2 was reached. A voluminous precipitate was obtained, which was centrifuged at 0°C. Analysis of the supernatant showed the presence of 84% albumin, with still about 4% of gamma globulins. The addition at 0°C of 10% alcohol by volume to the supernatant resulted in a second precipitation, which again was centrifuged off at the same temperature. The resulting supernatant then analyzed 95% albumin, and less than 0.5% gamma globulin.

EXAMPLE II

This example demonstrates the recovery through desalting of an albumin-enriched fraction from the so-called Cohn II + III supernatant fraction, obtained by precipitation of plasma with 18% alcohol. It also demonstrates the advantage of selective redissolution of part of the albumin, precipitated with the euglobulin-like fraction, and the effects of electrical resistance and pH on the purity of fractions thus obtained. Two liters of the Cohn II + III supernatant were desalted as in experiment I, and separated into 100 ml. aliquots. Each aliquot was processed separately, all liquids being kept at 0°C throughout, even during centrifugation.

After thorough desalting, the resistance of the protein solution was 240,000 ohms-cm, pH 5.2. In some samples the resistance was decreased by the addition of concentrated sodium chloride, which had but negligible effect on pH. In two samples the pH was raised by the addition of sodium hydroxide. This also resulted in a significant lowering of resistance. After these adjustments, all aliquot samples were centrifuged, decanted and the precipitate washed in half of the original volume of either distilled water, or an alcohol solution of indicated concentration. The precipitate was thoroughly resuspended in this wash, and the resulting suspension was again centrifuged. The supernatant is the 'recoverable albumin', while the residue is the precipitate. Data in Table I show the resulting albumin content in all fractions:

TABLE I

It can be readily seen that the purity of the recovered albumin is strongly influenced by the alcohol content of the suspension medium. While precipitates may still have relatively high albumin content, the loss of albumin, considering the small weight of the precipitate is less than 8% of total albumin, the recovery being in excess of 90% in all instances.

TABLE I

Effect of pH, resistance and alcohol content on purity of protein fractions.

| Sample No. | Spec. resistance (ohms-cm) | pH | Supernatant Alb. % | Wash % alcohol | Recovery % alb. | Precipitate % alb. |
|---|---|---|---|---|---|---|
| 1 | 240,000 | 5.2 | 95.5 | 15 | 93.1 | 70.5 |
| 2 | 240,000 | 5.2 | 95.3 | 10 | 95.9 | 62.5 |
| 3 | 240,000 | 5.2 | 95.8 | 5 | 91.0 | 35.0 |
| 4 | 240,000 | 5.2 | 97.0 | 0 | 85.2 | 37.4 |
| 5 | 100,000 | 5.3 | 94.6 | 0 | 81.4 | 35.4 |
| 6 | 45,000 | 5.3 | 96.0 | 0 | 83.5 | 33.4 |
| 7 | 21,000 | 5.3 | 92.8 | 0 | 79.5 | 27.5 |
| 8 | 10,000 | 5.3 | 92.1 | 0 | 71.2 | 2.5 |
| 9 | 6,300 | 5.3 | 96.2 | 0 | 62.4 | 9.2 |
| 10 | 58,000 | 5.4 | 94.9 | 0 | 74.6 | 3.1 |
| 11 | 30,000 | 5.7 | 91.2 | 0 | 60.2 | 3.2 |

EXAMPLE III

This example shows the effect of the temperature during the separation of the euglobulin-like precipitate from the alcohol-containing plasma. The starting material was the same as in experiment II, i.e. thoroughly desalted Cohn II + III supernatant. This was divided into 100 ml. aliquots, and centrifuged at the indicated (Table II) temperatures. All precipitates were resuspended in an equal volume of 10% alcohol in distilled water, and centrifuged a second time. This washing step was repeated a second time, giving a second recoverable albumin fraction and the final precipitate. All steps were carried out with strict control of temperature, as indicated, the data is reported in Table II.

TABLE II

| Sample | Percent albumin at the indicated temperatures | | | |
|---|---|---|---|---|
| | (0°C) | (5°C) | (10°C) | (15°C) |
| 1st supernatant | 97.7 | 94.0 | 91.8 | 85.5 |
| 1st recovery | 94.1 | 91.2 | 90.1 | 85.5 |
| 2nd recovery | 89.2 | 82.3 | 78.1 | 78.0 |
| Precipitate | 17.5 | 10.2 | 5.5 | 5.0 |

EXAMPLE IV

This example illustrates the application of the process of the invention for the preparation of an albumin concentrate, using the steps of desalting of an alcohol-containing plasma protein fraction, separation of a euglobulin-like protein precipitate, recovery of partially precipitated albumin by a washing process in 10% alcohol, and, finally, concentration, and further purification using forced-flow electrophoresis of the combined supernatants from the first euglobulin-like precipitation and recovered protein.

The starting material was 10 liters of so-called Cohn Fraction IV-1 supernatant which is a later intermediary step in the current scheme of alcohol fractionation. The starting material was first desalted as in Example I, using a five membrane-pair cell assembly. The precipitated euglobulin-like fraction was centrifuged and washed twice with one liter aliquots of a 10% solution of alcohol in distilled water. The supernatants of this albumin recovery step were combined with the supernatant from the first centrifugation. The combined supernatants were adjusted to pH 7.5 using sodium hydroxide and concentrated by forced flow electrophoresis, using an assembly of five cells of the type illustrated in FIG. 2, yielding a bottom concentrate of albumin and a top effluent fraction. The results of the fractionation are recorded in Table III.

TABLE III

The albumin concentrate had only 5% alcohol content, while the original feed, namely the Cohn fraction IV-1 had 40% alcohol content. Thus, the forced-flow concentration resulted in significant decrease of alcohol content due to dialysis. Desalting does not alter alcohol content.

TABLE III

Preparation of albumin concentrate from Cohn Fraction IV-I.

| Sample | Volume (L) | Proteins concentr. (gms/L) | Albumin % | Total Protein (gms) | Total Albumin (gms) | Yield Albumin % |
|---|---|---|---|---|---|---|
| Supply | 10 | 23.2 | 90.6 | 232 | 210 | — |
| Albumin | 1.25 | 167.5 | 96.5 | 209.4 | 200.8 | 95.7 |
| Precipit. | 0.4 | 54.6 | 40.3 | 21.9 | 8.8 | 4.2 |
| Effluent | 12 | .3 | 40.0 | 3.6 | 1.4 | 0.7 |

EXAMPLE V

This experiment illustrates the new methodology used to recover valuable fractions from presently rejected materials. The starting material were 2,000 gms of wet precipitate from the so-called step IV-4 of the Cohn alcohol fractionation scheme. This material contains mainly alpha and beta globulins, but also contains between 40 and 50% of albumin, which is presently wasted. This precipitate was suspended in 10 liters of water, and thoroughly desalted according to Example I. Then 1 liter of alcohol was added, while keeping the solution at 0°C. This resulted in formation of a copious precipitate. The supernatant was clarified by centrifugation, and was found to contain about 1.6% of albumin, at 90.5% purity. A total of 180 gms of albumin were recovered from the 2,000 gms of paste, having a total content of albumin of about 320 gms. Thus, over 50% of albumin normally wasted was recovered.

We claim:

1. A process for the fractionation of liquid solutions of protein mixtures selected from the group consisting of plasma, serum and fractions derived therefrom which includes the steps of (a) subjecting such solutions to electrodialysis in the pH range 4.8 to 6; (b) conducting said electrodialysis at temperatures below 15°C; (c) continuing said electrodialysis until the specific resistance of the resultant mixture exceeds 1000 ohm-cm and a fraction of said protein mixture precipitates; (d) separating the precipitate from the supernatant soluble protein solution; and (e) recovering said supernatant soluble protein solution.

2. The process according to claim 1 wherein the specific resistance of the resultant mixture upon completion of the electrodialysis is in the range 50,000 to 200,000 ohm-cm and the temperature is maintained below about 5°C.

3. The process according to claim 2 wherein, the desalting electrodialysis is conducted until the final pH $5.3 \pm 0.2$ is reached, this being the isoelectric point of euglobulin and/or euglobulin-like proteins.

4. The process according to claim 3 wherein the precipitated fraction separated at (d) is the euglobulin or euglobulin-like proteins in plasma.

5. The process according to claim 1 wherein said plasma derived protein mixture is an albumin-containing fraction obtained by the Cohn alcohol process of plasma fractionation, such as the Cohn II + III supernatant fraction, said fraction containing at least 20% alcohol content, whereby the euglobulin and euglobulin-like fraction caused to precipitate by the electrodialysis process and separated at (d) includes mainly alpha and beta globulins, thus resulting in greater purity of albumin in the recovered soluble protein fraction.

6. The process according to claim 5 wherein recovered desalted supernatant soluble protein solution from (e) is treated with alcohol to precipitate its proteins, consisting mainly of albumin.

7. The process according to claim 1 wherein the electrodialyzed solution or suspension is adjusted to a 10 to 20% of alcohol content, this alcohol content in electrodialyzed plasma or plasma-derived solutions or suspensions causing optimal fractionation of euglobulin or euglobulin-like proteins from supernatant soluble proteins, and resulting in higher albumin purity in the supernatant fraction and separating and recovering said supernatant fraction.

8. The process according to claim 5 wherein the recovered euglobulin or euglobulin-like material is partially redissolved in a 5 to 15% alcohol-containing solution and the resulting supernatant protein solution is combined with the recovered albumin-containing soluble protein fraction.

9. The process according to claim 1 wherein the recovered supernatant soluble protein solution from (e) is further treated by buffering at the pH range of optimum protein electrophoretic mobility and then treated by an electrofield separation step.

10. The process according to claim 9 wherein the electrofield separation step is an electrodecantation.

11. The process according to claim 9 wherein the electrofield separation step is a forced-flow electrophoresis step.

12. The process according to claim 1 wherein the precipitated fraction separated at (d) is redissolved by the addition of alkali solution to raise the pH to about 6 and then again electrodialyzing the redissolved precipitated fraction.

13. The process according to claim 9 wherein the buffers employed are amphoteric, these amphoteric buffers having high buffering capacity and contributing little to increasing the specific electrical conductivity of the solution.

14. The process according to claim 13 wherein said amphoteric buffer is selected from the group consisting of tris (hydroxymethyl) aminomethane, glycine, alanine, glycyl-glycine, diglycyl-glycine.

15. The process according to claim 9 wherein said buffered product of the dialysis step is divided during said electrofield separation process into a top and bottom effluents as a result of said separation process and the flow rates of said top and bottom effluents are maintained at a ratio of 8:1 to 15:1.

16. A process according to claim 1 for the preparation of an albumin concentrate suitable for use as a plasma extender which comprises the steps of treating plasma with alcohol to precipitate and eliminate the Cohn II and III fractions, subjecting the supernatant to electrodialysis at temperatures below about 5°C until all euglobulins and euglobulin-like fractions have been precipitated,
separating and recovering the precipitated fraction and the supernatant soluble protein solution, mixing the precipitated fractions in a 5 to 15% alcohol-containing solution, separating the residue from the supernatant to yield an albumin-rich supernatant, combining said albumin-rich supernatant liquid with supernatant soluble protein solution, buffering said combined liquids at the pH of optimum protein electrophoretic mobility and introducing said buffered liquid into an electrofield separation apparatus having an influent and top and bottom effluents, supplying an electrical potential to said apparatus to separate protein fractions contained in said buffered liquid between the top and bottom effluents and collecting the albumin concentrate from said bottom effluent.

17. The albumin concentrate prepared according to claim 16.

18. An albumin concentrate from plasma for use in the preparation of plasma extenders, consisting of at least 90% albumin, said concentrate being substantially free from ionic salts, euglobulins and euglobulin-like materials.

19. A process for the fractionation of aqueous protein solution mixtures from naturally occuring biological fluids which includes the step of (a) subjecting said solution mixtures to deionizing electrodialysis at a pH range of ± 0.2 of the isoelectric point of said mixtures and at temperatures below 15°C; (b) continuing said deionizing dialysis until substantially all ionizable salts are removed from said mixture as indicated by the specific resistance of said dialysate increasing to above 50,000 ohm/cm; (c) separating the precipitated protein-fraction which is insoluble in the resulting deionized supernatant soluble protein fraction solution.

20. The process according to claim 19 wherein said protein solution mixture is derived from the class of naturally occuring biological fluids in the group consisting of milk, whey, urine, spinal fluid, egg white, blood plasma, serum and mixtures thereof.

* * * * *